(12) United States Patent
Rauh et al.

(10) Patent No.: US 9,814,550 B2
(45) Date of Patent: Nov. 14, 2017

(54) METHOD FOR AUTOMATIC CALIBRATION OF DENTAL FURNACES AND DENTAL FURNACE WITH AUTOMATIC CALIBRATION

(71) Applicant: Vita Zahnfabrik H. Rauter GmbH & Co. KG, Bad Säckingen (DE)

(72) Inventors: Wolfgang Rauh, Bad Säckingen (DE); Michael Jochen Tholey, Bad Säckingen (DE); Vanik Jinoian, Stein (CH)

(73) Assignee: Vita Zahnfabrik H. Rauter GmbH & Co. KG, Bad Säckingen (DE)

( * ) Notice: Subject to any disclaimer, the term of this patent is extended or adjusted under 35 U.S.C. 154(b) by 479 days.

(21) Appl. No.: 14/136,188

(22) Filed: Dec. 20, 2013

(65) Prior Publication Data

US 2014/0162203 A1 Jun. 12, 2014

(30) Foreign Application Priority Data

Dec. 27, 2012 (EP) .................................... 12199532

(51) Int. Cl.
*A61C 13/20* (2006.01)
*F27B 17/02* (2006.01)
*G01J 3/50* (2006.01)

(52) U.S. Cl.
CPC ............ *A61C 13/20* (2013.01); *F27B 17/025* (2013.01); *G01J 3/508* (2013.01)

(58) Field of Classification Search
CPC ......... F27B 17/025; G01J 3/508; A61C 13/20
See application file for complete search history.

(56) References Cited

U.S. PATENT DOCUMENTS 4,654,794 A * 3/1987 O'Brien ................. A61C 19/10
356/326
4,828,117 A * 5/1989 Panzera ................. A61C 19/10
206/63.5
(Continued)

FOREIGN PATENT DOCUMENTS

EP 1650519 A1 4/2006
EP 2026027 A1 2/2009

OTHER PUBLICATIONS

Claus, "Ein einfacher Test zur Prufung des Brenngrades der Dentalkeramik", "A Simple Test for Examination of the Firing Degree of Dental Ceramics", Dent Lab: 45:245-248. (Translation 8 pages).

(Continued)

*Primary Examiner* — Nathaniel Herzfeld
(74) *Attorney, Agent, or Firm* — Christensen, Fonder, Dardi & Herbert PLLC; Curtis B. Herbert

(57) ABSTRACT

An embodiment of the invention is a method for automatic calibration of dental furnaces, there is made available a dental furnace comprising a control unit adapted to control the dental furnace for performing a firing process defined by firing process parameters such as e.g. the temperature and/or a temporal temperature curve and/or a temperature gradient and/or a vacuum in a firing chamber of the dental furnace. There is provided at least one calibration firing-object sample made of a dental material, where said dental material, after said calibration firing-object sample has been subjected to a calibration firing-object process with predetermined firing process parameters, has a defined desired color stored e.g. in the control unit. Further, a color measuring device is used which, for transmission of measurement signals and/or measurement results, is operatively connected to the control unit.

6 Claims, 1 Drawing Sheet

(56) References Cited

U.S. PATENT DOCUMENTS

| | | | | |
|---|---|---|---|---|
| 5,162,130 | A * | 11/1992 | McLaughlin | A61C 5/00 264/129 |
| 6,249,348 | B1 * | 6/2001 | Jung | G01J 1/0411 250/226 |
| 6,254,385 | B1 * | 7/2001 | Jung | A61B 5/0088 356/405 |
| 7,534,028 | B2 | 5/2009 | Jussel et al. | |
| 8,052,424 | B2 * | 11/2011 | Cameron | A61C 13/0022 433/203.1 |
| 8,388,223 | B2 | 3/2013 | Childress et al. | |
| 2005/0175949 | A1 * | 8/2005 | Grunenfelder | A61C 13/20 432/120 |
| 2007/0212667 | A1 * | 9/2007 | Jung | A61C 13/0004 433/223 |
| 2010/0047731 | A1 * | 2/2010 | Zubler | A61C 13/20 432/45 |

OTHER PUBLICATIONS

Thoely, "The System Y-TZP and Its Porcelain. The Interface and Firing Influences of the Porcelain on the "Chipping."" University of Otago, Dunedin, New Zealand, Thesis, 203 pages. (Aug. 2011).

\* cited by examiner

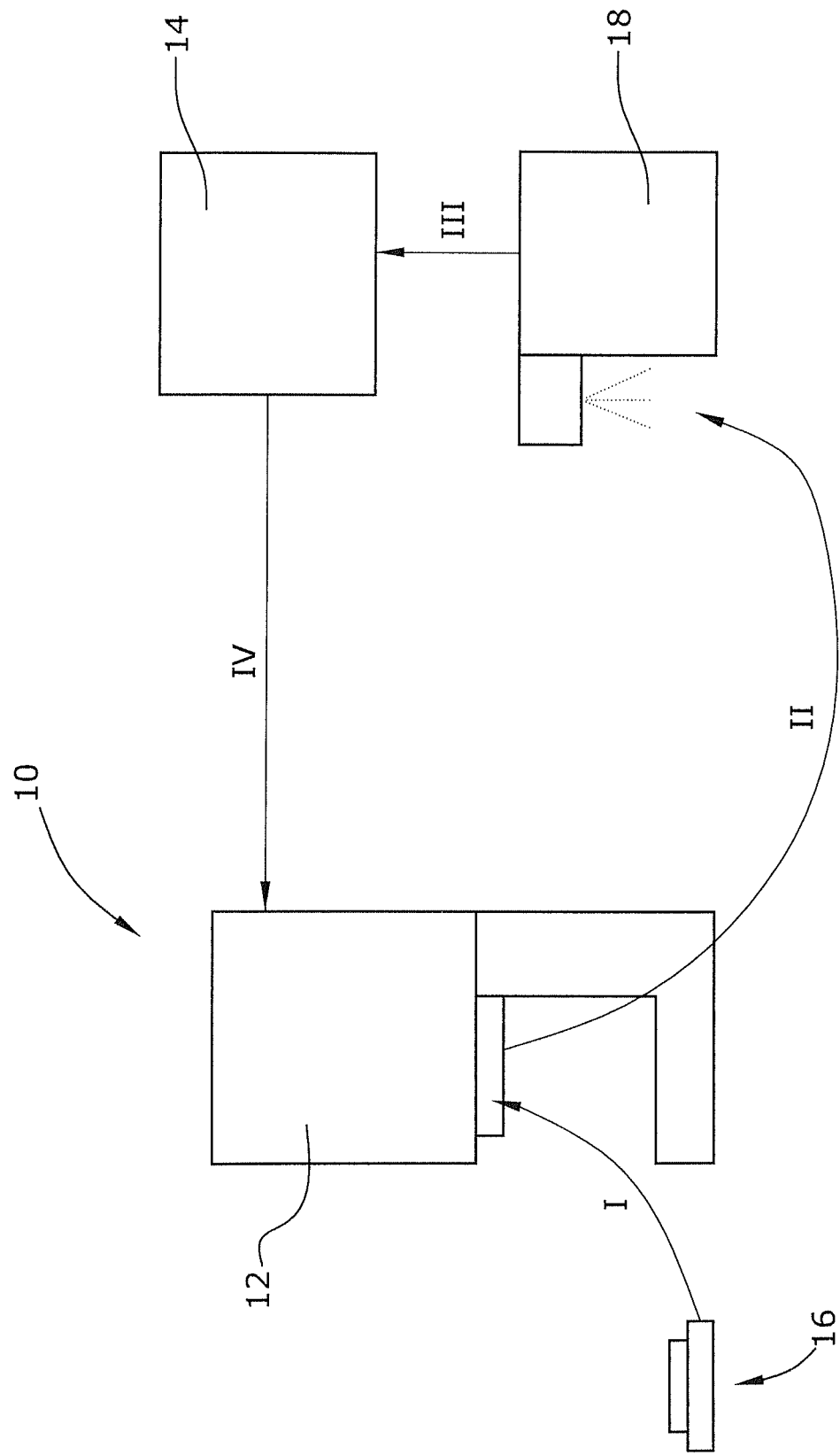

METHOD FOR AUTOMATIC CALIBRATION OF DENTAL FURNACES AND DENTAL FURNACE WITH AUTOMATIC CALIBRATION

CROSS REFERENCE TO RELATED APPLICATIONS

This Application claims priority to European Patent Application No. 12 199 532.8 filed on Dec. 27, 2012, the disclosure of which is hereby incorporated herein by reference.

BACKGROUND OF THE INVENTION

Technical Field

The technical field relates to a method for automatic calibration of dental furnaces and to a dental furnace with automatic calibration for the purpose of automatically setting at least one firing process parameter.

Background

The temperature of dental furnaces has an influence on the properties of the fired workpieces with respect to their glossiness, color, translucence and strength. For this reason, known dental furnaces have to be calibrated at regular intervals. This is performed with the aid of calibration firing-object samples which, if fired with correctly set firing process parameters, will lead to the desired, expected results with respect to glossiness, color, translucence and strength. Deviations of the actual result from the expected desired result will then be considered when re-adjusting the firing process parameters. In this regard, there is to be mentioned primarily the temperature of the dental furnace (change of the offset value of the temperature) which has to be re-adjusted. The above described process is performed manually and thus is bothersome.

A dental furnace with calibrating device is known e.g. from EP 1 650 519. In EP 2 026 027, the monitoring of the temperature for a dental furnace is described.

SUMMARY

Methods and devices that facilitate the calibration of dental furnaces are presented herein.

An embodiment of the invention is a method for automatic calibration of dental furnaces wherein, in this method
- a dental furnace is provided, said dental furnace comprising a control unit adapted to control the dental furnace for performing a firing process defined by firing process parameters such as e.g. the temperature and/or a temporal temperature curve and/or a temperature gradient and/or a vacuum in a firing chamber of the dental furnace,
- at least one calibration firing-object sample made of a dental material is provided, where said dental material, after said calibration firing-object sample has been subjected to a calibration firing-object process with predetermined firing process parameters, has a defined desired color,
- a color measuring device is provided which, for transmission of measurement signals or measurement results, is operatively connected to the control unit,
- said calibration firing-object sample is subjected to the calibrating firing process in the dental furnace,
- the fired calibration firing-object sample is measured by means of the color measuring device,
- a target/actual comparison (i.e. a comparison between a desired and an actual value) is performed between the defined desired color and the metrologically detected actual color of the fired dental material of the calibration firing-object sample, and
- in accordance with a deviation and/or the degree of a deviation of the actual color from the desired color, at least one of the firing process parameters is calibrated and the calibrated firing process parameter is stored for use under control of the control unit,
- wherein, for calibration of the at least one firing process parameter, use is made of an automatically readable table containing different values for the at least one firing process parameter and respective values of actual colors assigned to these values, which coordinates have been obtained in preceding tests when firing calibration firing-object samples of substantially identical material properties and geometric shapes with use of the different values for the at least one firing process parameter, preferably in the dental furnace which is to be calibrated or in a comparable dental furnace (e.g. identical model, identical series or identical type) or in another dental furnace whose firing properties are in a known relationship to the dental furnace which is to be calibrated.

According to an embodiment of the invention, a color measuring device is coupled, preferably according to the photospectrometric principle, to the control unit of a dental furnace so that the measurement results and/or the comparison results obtained with the aid of the color measuring device will be directly received by the control unit of the dental furnace. Either in the color measuring device or in the control unit or in a unit which is accessible at least by the control unit, a target/actual comparison is performed particularly of the color of a calibration firing-object sample after the firing process. Deviations and/or the size or the extent, i.e. the degree of a deviation will be automatically converted into a calibration of the respective firing process parameter, wherein the calibrated firing process parameter will then be automatically stored e.g. in the control unit or generally in an automatically readable data memory and be used for the subsequent burning processes until the next calibration of the dental furnace will be carried out. According to the inventions, this is performed by use of a table, wherein, for calibration of the at least one firing process parameter, use is made of an automatically readable table containing different values for the at least one firing process parameter and respective values of actual colors assigned to these values, which coordinates have been obtained in preceding tests when firing calibration firing-object samples of substantially identical material properties and geometric shapes with use of the different values for the at least one firing process parameter, preferably in the dental furnace which is to be calibrated or in a comparable dental furnace (e.g. identical model, identical series or identical type) or in another dental furnace whose firing properties are in a known relationship to the dental furnace which is to be calibrated. The preceding measurement series provided for later calibration of a dental furnace are preferably performed by means of a dental furnace which is identical to—or of a similar nature as—the dental furnace which is to be calibrated later, particularly with respect to the technical, physical and constructional properties of the firing chamber. In this regard, for instance, the measurement series could be performed by use of a dental furnace to which the dental furnaces to be calibrated later are constructionally identical (identical model, identical type etc.), or the dental furnaces to be calibrated later could be in a known relation, with regard to the firing properties, to the dental furnace by which the measurement series was (were) performed.

In the framework of the present invention, the color comprises the definition of at least one of the following parameters: color in the actual sense, color saturation, shade of color, brightness of color, translucence and glossiness. Consequently, the color measuring device is capable of metrologically detecting at least one of these parameters.

An embodiment of the invention is a method for automatic calibration of dental furnaces, there is made available a dental furnace comprising a control unit adapted to control the dental furnace for performing a firing process defined by firing process parameters such as e.g. the temperature and/or a temporal temperature curve and/or a temperature gradient and/or a vacuum in a firing chamber of the dental furnace. There is provided at least one calibration firing-object sample made of a dental material, where said dental material, after said calibration firing-object sample has been subjected to a calibration firing-object process with predetermined firing process parameters, has a defined desired color stored e.g. in the control unit. Further, a color measuring device is used which, for transmission of measurement signals and/or measurement results, is operatively connected to the control unit. In the method, a calibration firing-object sample is subjected to the calibrating firing process in the dental furnace, and the fired calibration firing-object sample is then measured by means of the color measuring device. A target/actual comparison is performed, e.g. in the control unit, between the defined desired color and the metrologically detected actual color of the fired dental material of the calibration firing-object sample. In accordance with a deviation and/or the degree of a deviation of the actual color from the desired color, at least one of the firing process parameters is calibrated and the calibrated firing process parameter is stored e.g. in the control unit.

An embodiment of the invention is making and/or using a dental furnace comprising
  a combustion chamber,
  a control unit for automatically performing a firing process in the combustion chamber with use of firing process parameters such as e.g. the temperature and/or a temporal temperature curve and/or a temperature gradient and/or a vacuum in the combustion chamber, and
  a color measuring device which, for transmission of measurement signals and/or measurement results with respect to color and/or translucence, is operatively connected to the control unit,
  at least one of the firing process parameters being adapted to be automatically calibrated and respectively being calibrated on the basis of a target/actual comparison of the color, particularly of the color saturation, the shade of color and/or the brightness of color, and/or the translucence of a calibration firing-object sample, notably by use of an automatically readable table containing different values for the at least one firing process parameter and respective values of actual colors assigned to these values, which coordinates have been obtained in preceding tests when firing calibration firing-object samples of substantially identical material properties and geometric shapes with use of the different values for the at least one firing process parameter.

According to a further advantageous variant of the invention, it can be provided that the color measuring device is a digital color measuring device. In this regard, it does not play a role which color space is used as a basis in the color measuring device. Color measurements will normally result in a triplet of values, i.e. in three parameters; there exist a plurality commonly used color spaces such as e.g. LMS, XYZ, RGB, CMYK, HSV, Lab, I1I2I3, YCbCr, xvYCC, YPrPb, YUV, YIQ, YDbDr and YCC According to a further advantageous variant of the invention, it is provided that the desired color is defined by a desired brightness, a desired saturation and a desired shade of color and that the color measurement comprises the metrological detection of brightness, saturation and shade of color of the fired material of the calibration firing-object sample.

As already mentioned above, the temperature (preferably the maximum temperature) to which the firing chamber shall be heated according to a predetermined firing process, is particularly suited for use as a firing process parameter to be subjected to calibration, wherein, in this case, the firing process parameter is a temperature offset value by which there will be corrected the measurement value of a temperature sensor provided to detect the temperature in the firing chamber of the dental furnace.

Finally, apart from the color of the fired calibration firing-object sample, also the translucence and/or glossiness of the latter can be detected in order to allow for conclusions on possible incorrect settings and respectively on firing process parameters which are to be calibrated. In this regard, it is provided according to the invention that the color measurement comprises the metrological detection of the translucence and/or glossiness of the fired dental material of the calibration firing-object sample, and that a deviation or degree of deviation of the actual translucence from the desired translucence and/or of the actual glossiness from the desired glossiness of the fired dental material of the firing-object sample makes it possible to conclude on a required calibration of the furnace.

Further, it is rendered possible to detect local differences in temperature in the firing furnace by performing measurements at different sites of the calibration firing-object sample.

Thus, according to the invention, there is used a digital color measuring device, particularly of the electronic type, whose measurement values are incorporated in the control of the dental furnace. Further, use is made of harmonized/standardized calibration firing-object samples and a harmonized firing program for firing these samples so as to determine deviations in color (and optionally deviations in translucence) of the fired firing-object samples from the color/translucence/glossiness to be expected under optimal conditions. Further, the invention comprises the automatic feedback of the color and/or translucence and/or glossiness deviation information into the furnace control in order to correct at least one firing process parameter (particularly the firing temperature and, put more precisely, the temperature offset value).

For applying the invention in a dental furnace, the furnace comprises a furnace control unit, a digital color measuring device, an interface between the color measuring device and the furnace control unit for transmission of color information (and optionally translucence and glossiness information), and software (e.g. in the furnace control unit) for determining the deviation (and/or the extent thereof) between measured actual color values and stored desired color values (which correspondingly holds true also for the translucence and the glossiness), and for automatic adaptation of the furnace parameters.

Realizations of various embodiments of the invention comprise:
- the use of standard materials with pre-stored target color and/or target translucence values and/or and target glossiness values,
- the use of premium test bodies (performs from "calibrated" batches) which are delivered e.g. with calibrated desired values (and, depending on the given case, have to be input into the software by the user), and
- the definition of the desired values by the user (while there should be always used the same material) so as to always return the dental furnace back into the desired, self-defined state, wherein there are performed a firing process with a specific material, subsequent measurement, subsequent transmission and storage of the reference values.

A useful feature of the invention resides in the automatic correction of primarily or exclusively the firing temperature of the furnace. The heat-up rate and the dwelling time at the firing temperature are of inferior importance because they represent a control of the temperature difference (i.e. particularly no absolute measurement of the temperature) over time and because, due to highly precise clock generators in the microprocessor controls of the furnaces, the time measurement is not affected by deviations that would be relevant in practice. The same holds true for the cool-down-rate of the furnaces. In contrast thereto, the absolute value of the firing temperature plays a decisive role for the visual appearance of the ceramic firing object (see e.g. Claus H., Ein einfacher Test zur Prüfung des Brenngrades der Dentalkeramik. Dent Lab 1997; 45; 245-248, and Thoely, M., The system Y-TZP and its porcelain. The interface and firing influences of the porcelain on the "chipping". University of Otago, Dissertation, 2012).

The importance of the invention is to be seen in the fact that the temperatures used for the firing of ceramic materials have a significant influence on the physical properties (e.g. breaking strength) of the firing object. The visual appearance, however, allows for conclusions on the temperature which is effective for the firing, so that the temperature can be corrected, if required, and the dental furnace can be calibrated.

Deviations of the real, measured firing temperature $T_{mess}$ in the furnace from the set (ideal) firing temperature $T_{Anzeige}$ can be caused e.g. by aging of the thermocouple for measuring the temperature in the firing chamber. Further, even when the ideal firing chamber temperature has been reached, deviations of the optical (and other physical) properties of the firing object can be caused by use of different support materials for the firing object ("firing trays") or by different heights of the firing object in the furnace.

The visual appearance of a body is composed of the color coordinates, classically referred to as color, and of the values for light transmission which are likewise detectable from colorimetrical measurements ("translucence"), and the glossiness of the sample. For the quantifying of the color, it is totally irrelevant which color space is used. The color properties of a body can be described in various coordinate systems (color spaces) which can be transferred into each other by mathematical transformations. In the present application, use is made preferably of the Lab system while this is not at all obligatory because the systems are deemed to be of equal usefulness. Neither translucence nor glossiness are contained in the color coordinates. For the present invention, there are used the lab color coordinates and optionally also the glossiness and the translucence and possibly further optical properties.

For setting the burning temperature, the following approach is provided according to a variant of the invention:

a) firing a firing-object sample made of a ceramic material specially produced and enclosed by the manufacturer for this purpose, with use of burning parameters predefined therefor which in their entirety constitute a firing program and have been stored as such e.g. in the control unit of the furnace.

b) Measuring the color coordinates (L, a, b) of the firing-object sample and optionally of the translucence and/or the glossiness of the firing-object sample and possibly of further parameters by use of a suitable color measuring device. Suitable devices for this purpose are photospectrometers which comprise corresponding illumination devices and evaluation software.

c) Determining the actual firing temperature $T_{mess}$ in the furnace from the n measured optical values (e.g. n=3 color coordinates) with use of the tables obtained from a previous measurement series (see below under item e). Particularly, for this purpose, use can be made of a method for minimizing the error sum of squares.

It be assumed that $M_1, M_2, M_3 \ldots M_n$ are the n measured optical parameters of the firing-object sample and $P_1(T_j), P_2(T_j), P_3(T_j), \ldots P_n(T_j)$ the n values, available as tabular data, of the optical parameters at the temperatures $T_j$ (j=1, \ldots, m). The real firing temperature $T_{mess}$ will then result from $$T_{Mess} = \min_j \sum_{i=1}^{n} a_i * (M_i - P_i(T_j))^2$$

wherein $a_i$ are weighting factors for the individual parameters which serve for adaptation of the different range of values and for the different weighting of the parameters.

d) Derivation of a correctional value for the firing temperature in the furnace. The correctional value results from $$T_{korr} = T_{Mess} - T_{Anzeige}$$

e) The measurement series mentioned above under c) is performed e.g. as follows:

From a ceramic material mentioned under a), identical test bodies are produced, and these are fired in the same, identically designed furnaces which are controlled and monitored with high precision, while using different firing temperatures $T_j$. Of all test bodies, the optical properties which will be used later are measured and are stored in tabular form according to the temperature $T_j$. The corresponding tables will be used in the later measurement process in order to determine the real firing temperature in the furnace.

f) The tables can be established based on the firing of the test bodies with different combinations of at least two and preferably more firing parameters. In doing so, the measured color coordinates will be stored in tabular form in accordance with the plurality of firing parameters which within the one or plural measurement series have been selected to have different amounts. Thus, the dental furnace can be calibrated with respect to a plurality of firing parameters.

BRIEF DESCRIPTION OF THE DRAWINGS

FIG. 1 depicts an embodiment of the invention that involves using a furnace comprising a firing chamber controllable by a control unit.

DETAILED DESCRIPTION OF PREFERRED EMBODIMENTS

A full and enabling disclosure of the present invention, enabling one of ordinary skill in the art to carry out the invention, is set forth in greater detail in the following description, including reference to the accompanying drawing in which FIG. 1 shows an embodiment of the invention.

Referring to FIG. 1, reference numeral 10 denotes a dental furnace comprising a firing chamber 12 which is controllable by a control unit 14 in accordance with a desired firing process. This control process of the firing chamber 12 comprises the adjustment of the (maximum) temperature of firing chamber 12, a possibly required evacuation and a predetermined temperature curve.

A calibration firing-object sample 16 is fired in firing chamber 12 according to a predetermined firing process (see step I in FIG. 1). After the firing process, the color and/or translucence and/or glossiness of the fired calibration firing-object sample is measured with the aid of an electronic, digital color measuring device 18 (see step II in FIG. 1). The measurement results of the color measuring device are transmitted to control unit 14 according to step III in FIG. 1. Either in control unit 14 or in said color measuring device 18, a target/actual comparison is performed between the measured color and/or translucence and/or glossiness and, e.g., color and/or translucence and/or glossiness values stored in an automatically readable data memory. Deviations will lead to an automatic calibration of the firing process parameters responsible for the deviation, so that a subsequent firing process can be automatically performed by control unit 14 by use of the calibrated firing process parameters that have been stored in an automatically readable data memory (see step IV in FIG. 1).

Although the invention has been described and illustrated with reference to specific illustrative embodiments thereof, it is not intended that the invention be limited to those illustrative embodiments. Those skilled in the art will recognize that variations and modifications can be made without departing from the true scope of the invention as defined by the claims that follow. It is therefore intended to include within the invention all such variations and modifications as fall within the scope of the appended claims and equivalents thereof.

The invention claimed is:

1. A method for automatic calibration of a dental furnace comprising
providing a dental furnace, said dental furnace comprising a control unit adapted to control the dental furnace for performing a firing process defined by firing process parameters,
providing at least one calibration firing-object sample made of a dental material, wherein said dental material, after said calibration firing-object sample has been subjected to a calibration firing-object process with predetermined firing process parameters, has a defined desired color,
providing a color measuring device which, for transmission of measurement signals or measurement results, is operatively connected to the control unit,
with said calibration firing-object sample being subjected to the calibrating firing process in the dental furnace, with the fired calibration firing-object sample being measured by means of the color measuring device,
performing a target/actual comparison between the defined desired color and the metrologically detected actual color of the fired dental material of the calibration firing-object sample, and
in accordance with a deviation and/or a degree of a deviation of the actual color from the desired color, at least one of the firing process parameters is calibrated and the calibrated firing process parameter is stored for use under control of the control unit,
wherein, for calibration of the at least one firing process parameter, a use is made of an automatically readable table containing different values for the at least one firing process parameter and respective values of actual colors assigned to these values, which coordinates have been obtained in preceding tests when firing calibration firing-object samples of substantially identical material properties and geometric shapes with use of the different values for the at least one firing process parameter, with the automatic calibration of the furnace establishing colors that are actually achieved when operating the furnace with the at least one firing process parameter that is calibrated for the provided dental furnace.

2. The method of claim 1 wherein the process parameters comprise at least one member selected from the group consisting of temperature, a temporal temperature curve, a temperature gradient, and a vacuum in a firing chamber of the dental furnace.

3. The method according to claim 1, wherein the desired color is defined by desired brightness, a desired saturation and a desired shade of color, and wherein the color measurement comprises the metrological detection of brightness, saturation and shade of color of the fired dental material of the calibration firing-object sample.

4. The method according to claim 1, wherein said at least one firing process parameter is a temperature offset value for use in correcting the measurement value of a temperature sensor detecting the temperature in the firing chamber of the dental furnace.

5. The method according to claim 1 wherein the desired color is also defined by a desired translucence and/or a desired glossiness, the color measurement comprises the metrological detection of the translucence and/or glossiness of the fired dental material of the calibration firing-object sample, and wherein a deviation or degree of deviation of the actual translucence from the desired translucence and/or of the actual glossiness from the desired glossiness of the fired dental material of the firing-object sample makes it possible to conclude on a required calibration of the vacuum and/or that, in case of such a deviation, a firing process parameter is calibrated.

6. The method according to claim 1, wherein the desired color is also defined by a desired glossiness, that the color measurement comprises the metrological detection of the glossiness of the fired dental material of the calibration firing-object sample, and wherein a deviation and/or degree of deviation of the actual glossiness from the desired glossiness of the fired dental material of the firing-object sample makes it possible to conclude on a required calibration and/or that, in case of such a deviation, a firing process parameter is calibrated.

* * * * *